(12) United States Patent
Kwok et al.

(10) Patent No.: US 12,638,187 B2
(45) Date of Patent: May 26, 2026

(54) PORTABLE HEATER WITH SAFETY FEATURES

(71) Applicant: Pinnacle Climate Technologies, Inc., Eden Prairie, MN (US)

(72) Inventors: Chris Kwok, Sartell, MN (US); Jacob Frame, St. Joseph, MN (US); Mark Daniels, St. Cloud, MN (US)

(73) Assignee: Pinnacle Climate Technologies, Inc., Eden Prairie, MN (US)

( * ) Notice: Subject to any disclaimer, the term of this patent is extended or adjusted under 35 U.S.C. 154(b) by 527 days.

(21) Appl. No.: 18/163,013

(22) Filed: Feb. 1, 2023

(65) Prior Publication Data

US 2023/0243510 A1 Aug. 3, 2023

Related U.S. Application Data

(60) Provisional application No. 63/305,554, filed on Feb. 1, 2022.

(51) Int. Cl.
*F24H 15/345* (2022.01)
*F24C 5/16* (2006.01)
(Continued)

(52) U.S. Cl.
CPC .................. *F24C 5/16* (2013.01); *F24C 5/20* (2013.01); *G01N 33/0062* (2013.01)

(58) Field of Classification Search
CPC .... F24C 5/16; F24C 5/20; F24H 3/065; F24H 15/414; F24H 9/2085; F24H 3/006; F24H 3/02; F24H 3/025
See application file for complete search history.

(56) References Cited

U.S. PATENT DOCUMENTS 4,108,143 A * 8/1978 Pelsue ..................... F24H 3/065
126/110 B
5,165,883 A 11/1992 Van Bemmel
(Continued)

FOREIGN PATENT DOCUMENTS

AU 2020227096 A1 * 3/2021 ........... F24H 3/0417
CN 108548322 A * 9/2018
(Continued)

*Primary Examiner* — Gregory A Wilson
(74) *Attorney, Agent, or Firm* — Merchant & Gould P.C.

(57) ABSTRACT

A fuel-fired heater can include a fuel tank; a housing assembly supported by the fuel tank, the housing assembly defining a chamber having an inlet and an air outlet; a fan located within the housing assembly; an air pump located within the housing assembly; an electric motor coupled to at least one of the fan and the air pump; a burner assembly located within the housing assembly, the burner assembly including a burner nozzle in fluid communication with the air pump and the fuel tank via a fuel line, and including an ignitor; and an electronic controller operating the electric motor and ignitor, the electronic controller including a proximity sensor oriented and arranged to sense an object located in front of the air outlet, wherein the electronic controller deactivates the electric motor when an object is sensed by the proximity sensor within a predetermined distance for a predetermined time period. In some examples, the heater includes a carbon monoxide sensor oriented and arranged to sense an ambient carbon monoxide level proximate the heater, wherein the electronic controller closes the fuel shut-off valve when a sensed carbon monoxide level exceeds a predetermined threshold for a predetermined period of time, for example 180 seconds. In some examples, the heater includes a fuel shut-off valve oriented and arranged to control fuel flow in the fuel line, wherein the electronic controller deactivates the heater by first activating the fuel shut-off valve to block flow through the fuel line and (Continued)

subsequently deactivating the electric motor after a predetermined time period.

20 Claims, 12 Drawing Sheets

(51) Int. Cl.
  *F24C 5/20* (2021.01)
  *G01N 33/00* (2006.01)

(56) References Cited

U.S. PATENT DOCUMENTS

| | | | |
|---|---|---|---|
| 5,805,767 A | 9/1998 | Jouas et al. | |
| 5,807,098 A * | 9/1998 | Deng | F23N 5/242 |
| | | | 432/36 |
| 8,893,706 B2 * | 11/2014 | Vandrak | F24H 3/0488 |
| | | | 126/93 |
| 8,950,390 B2 * | 2/2015 | Froese | F23L 15/00 |
| | | | 126/104 A |
| 9,317,046 B2 * | 4/2016 | Gum | F24H 1/46 |

| | | | |
|---|---|---|---|
| 10,015,655 B2 | 7/2018 | Doorandish | |
| 10,648,696 B2 | 5/2020 | Milfeldt | |
| 10,876,744 B2 * | 12/2020 | Batson | F24D 19/1084 |
| 2008/0302351 A1 * | 12/2008 | Hunter | F24H 3/0488 |
| | | | 126/110 B |
| 2010/0032424 A1 * | 2/2010 | Cameron | F24H 9/0063 |
| | | | 219/386 |
| 2019/0145663 A1 * | 5/2019 | Huggins | F24H 15/345 |
| | | | 392/365 |
| 2020/0400345 A1 * | 12/2020 | Haak | F24H 15/281 |
| 2021/0080112 A1 | 3/2021 | Vandrak et al. | |
| 2021/0325050 A1 * | 10/2021 | Vie | F24H 15/31 |
| 2021/0396139 A1 | 12/2021 | Erisgen et al. | |

FOREIGN PATENT DOCUMENTS

| | | | | | |
|---|---|---|---|---|---|
| CN | 111964044 A | * | 11/2020 | | |
| EP | 3093578 B1 | * | 12/2018 | | F24H 3/006 |
| KR | 101931441 B1 | * | 12/2018 | | |
| KR | 20200119942 A | * | 10/2020 | | |
| KR | 20230067772 A | * | 5/2023 | | |
| WO | 2007035928 A2 | | 3/2007 | | |

* cited by examiner

100

214

PORTABLE HEATER WITH SAFETY FEATURES

RELATED APPLICATION

This application claims priority to U.S. Provisional Patent Application Ser. No. 63/305,554 filed on Feb. 1, 2022, the entirety of which is incorporated by reference herein.

BACKGROUND

Portable heaters, for example, portable kerosene heaters having an integrated fuel tank, are known. Portable heaters are used for a variety of purposes, such as providing heating on construction sites when outdoor ambient temperatures are below acceptable temperatures for the workers and/or the materials and systems being installed. Portable heaters having various safety features are desirable. Different safety features can be desirable depending on the situation the portable heater. A portable heater capable of having different and configurable safety features is desired.

SUMMARY

A fuel-fired heater can include a fuel tank; a housing assembly supported by the fuel tank, the housing assembly defining a chamber having an inlet and an air outlet; a fan located within the housing assembly; an air pump located within the housing assembly; an electric motor coupled to at least one of the fan and the air pump; a burner assembly located within the housing assembly, the burner assembly including a burner nozzle in fluid communication with the air pump and the fuel tank via a fuel line, and including an ignitor; and an electronic controller operating the electric motor and ignitor, the electronic controller including a proximity sensor oriented and arranged to sense an object located in front of the air outlet, wherein the electronic controller deactivates the electric motor when an object is sensed by the proximity sensor within a predetermined distance for a predetermined time period.

In some examples, the heater includes a carbon monoxide sensor oriented and arranged to sense an ambient carbon monoxide level proximate the heater, wherein the electronic controller causes the fuel shut-off valve to close when a sensed carbon monoxide level exceeds a predetermined threshold for a predetermined period of time and subsequently deactivating the electric motor after a predetermined time period.

In some examples, the heater includes a fuel shut-off valve oriented and arranged to control fuel flow in the fuel line, wherein the electronic controller deactivates the heater by first activating the fuel shut-off valve to block flow through the fuel line and subsequently deactivating the electric motor after a predetermined time period.

In some examples, the proximity sensor is mounted to the housing assembly.

In some examples, the electronic controller generates an audio warning when an object is sensed by the proximity sensor at a first predetermined distance.

In some examples, the first predetermined distance is within 0.5 to 1.5 feet of the housing assembly air outlet.

In some examples, the electronic controller immediately closes the fuel shut-off valve when an object is sensed by the proximity sensor at a distance between 0 and 0.5 feet from the housing assembly air outlet.

In some examples, the proximity sensor is an ultrasound or infrared type proximity sensor.

In some examples, the predetermined threshold is 50 to 200 parts per million of carbon monoxide.

In some examples, the predetermined time period is between one and five minutes.

In some examples, the predetermined time period is about three minutes.

A fuel-fired heater can include a fuel tank; a housing assembly supported by the fuel tank, the housing assembly defining a chamber having an inlet and an air outlet; a fan located within the housing assembly; an air pump located within the housing assembly; an electric motor coupled to at least one of the fan and the air pump; a burner assembly located within the housing assembly, the burner assembly including a burner nozzle in fluid communication with the air pump and the fuel tank via a fuel line, and including an ignitor; a fuel shut-off valve oriented and arranged to control fuel flow in the fuel line; and an electronic controller operating the electric motor, ignitor, and fuel shut-off valve, the electronic controller including a shut-down sequence in which the electronic controller deactivates the heater by first activating the fuel shut-off valve to block flow through the fuel line and subsequently deactivating the electric motor after a predetermined time period.

In some examples, the predetermined time period is between one and five minutes.

In some examples, the predetermined time period is about three minutes.

In some examples, the heater includes a proximity sensor oriented and arranged to sense an object located in front of the air outlet, wherein the electronic controller activates the shut-down sequence or immediately deactivates the electric motor when an object is sensed by the proximity sensor within a predetermined distance for a predetermined time period.

In some examples, the proximity sensor is mounted to the housing assembly.

In some examples, the electronic controller generates an audio warning when an object is sensed by the proximity sensor at a first predetermined distance.

In some examples, the first predetermined distance is within 0.5 to 1.5 feet of the housing assembly air outlet.

In some examples, the electronic controller immediately shuts down the electric motor when an object is sensed by the proximity sensor at a distance between 0 and 0.5 feet from the housing assembly air outlet.

In some examples, the proximity sensor is an ultrasound or infrared type proximity sensor.

In some examples, a carbon monoxide sensor oriented and arranged to sense an ambient carbon monoxide level proximate the heater, wherein the electronic controller activates the shut-down sequence when a sensed carbon monoxide level exceeds a predetermined threshold for a predetermined period of time.

In some examples, the predetermined threshold is 50 to 200 parts per million of carbon monoxide.

A variety of additional aspects will be set forth in the description that follows. The aspects can relate to individual features and to combinations of features. It is to be understood that both the forgoing general description and the following detailed description are exemplary and explanatory only and are not restrictive of the broad inventive concepts upon which the examples disclosed herein are based.

BRIEF DESCRIPTION OF THE DRAWINGS

The accompanying drawings, which are incorporated in and constitute a part of the description, illustrate several aspects of the present disclosure. A brief description of the drawings is below.

DETAILED DESCRIPTION

Figure 1:
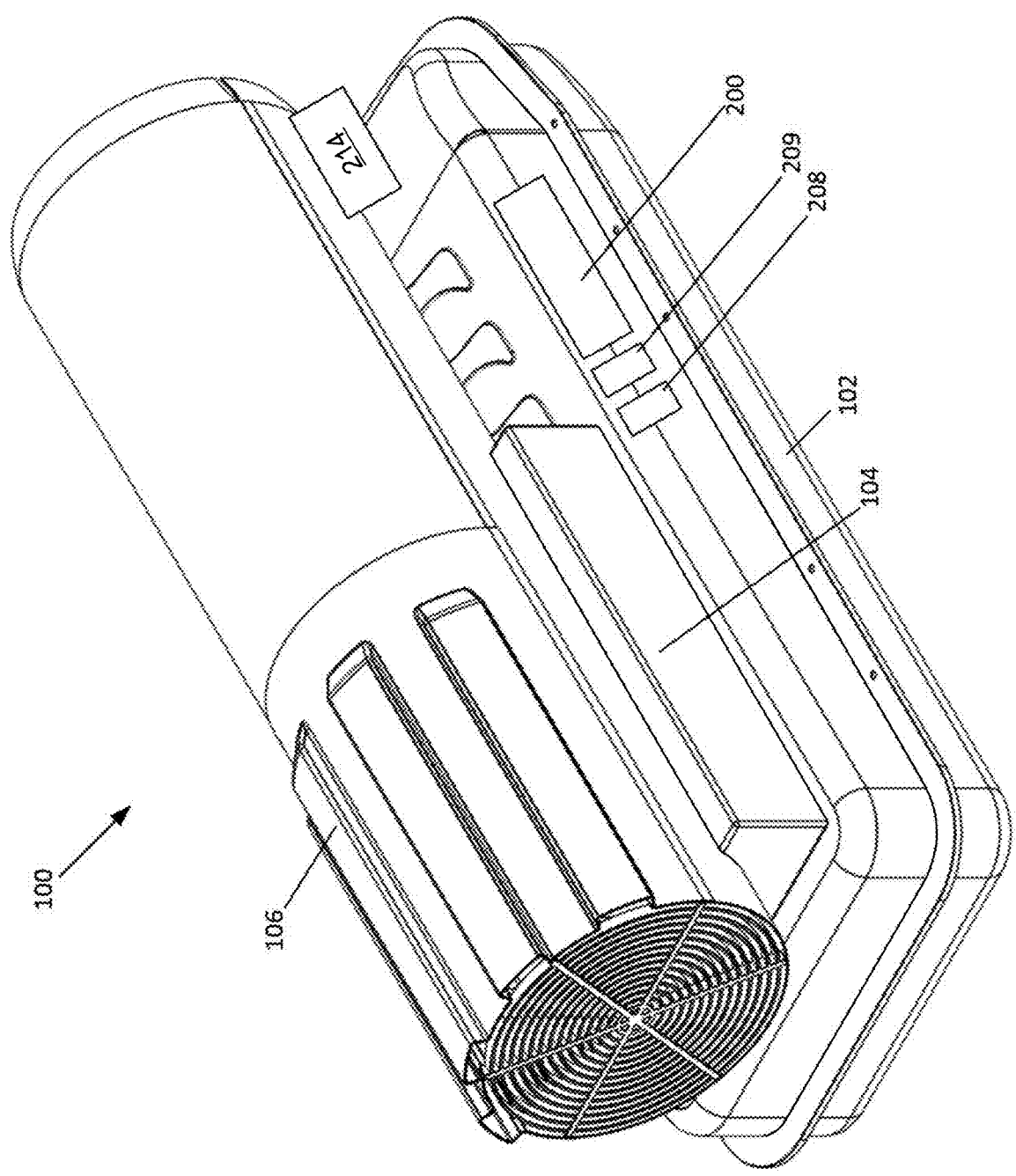
FIG. 1 is a perspective view of a portable heater having features in accordance with the present disclosure.

Various examples will be described in detail with reference to the drawings, wherein like reference numerals represent like parts and assemblies throughout the several views. Reference to various examples does not limit the scope of the claims attached hereto. Additionally, any examples set forth in this specification are not intended to be limiting and merely set forth some of the many possible examples for the appended claims. Referring to the drawings wherein like reference numbers correspond to like or similar components throughout the several figures.

Figure 2:
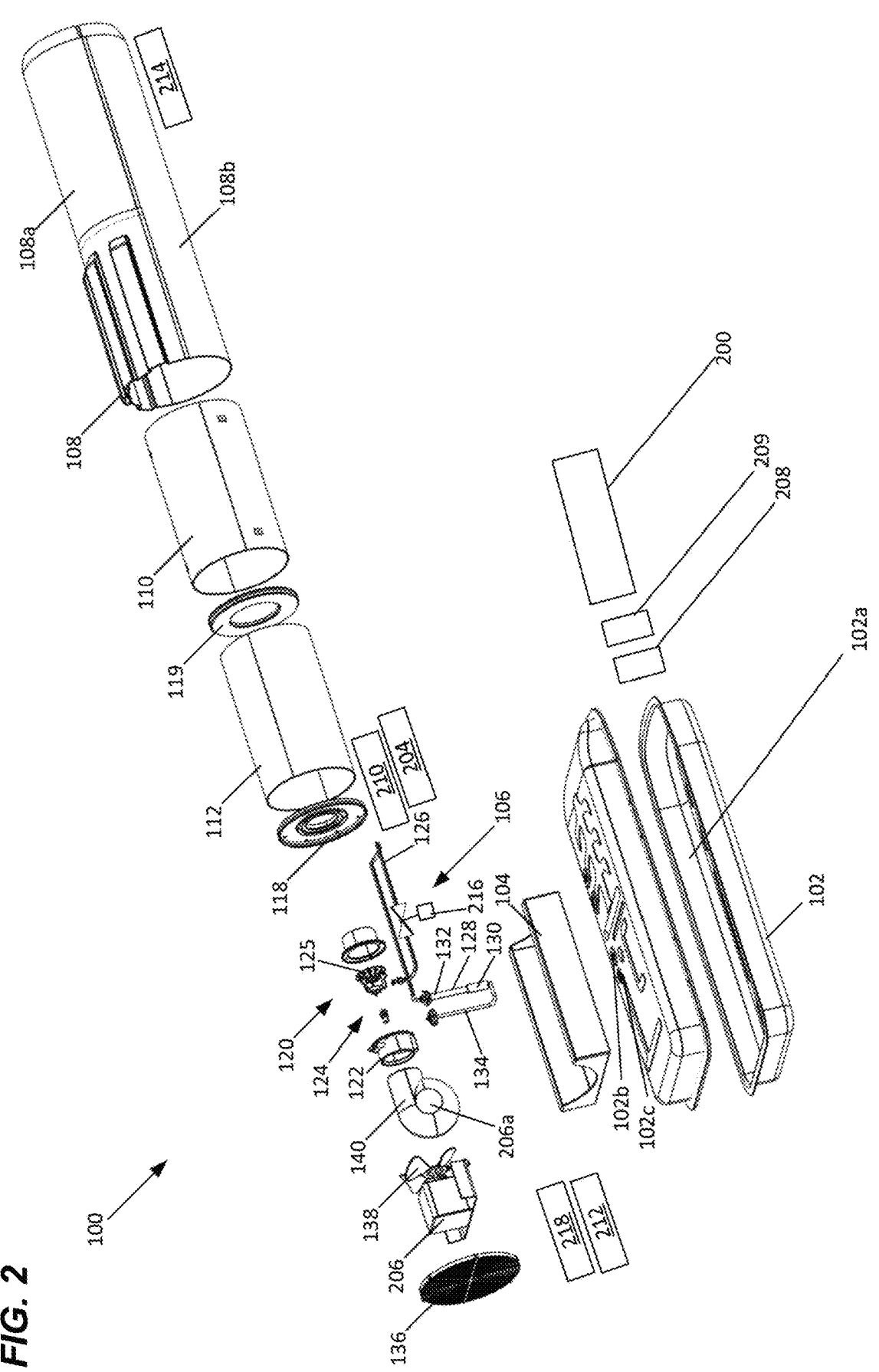
FIG. 2 is an exploded perspective view of the portable heater shown in FIG. 1.

Referring to FIGS. 1 and 2, a portable heater 100 is shown. As shown, the portable heater 100 includes a fuel tank 102 defining an interior volume 102a within which liquid fuel, for example kerosene or diesel, can be stored. The portable heater 100 is also shown as including a base frame 104 and a heater assembly 106. The base frame 104 is mounted to the fuel tank 102 and supports the heater assembly 106. The portable heater 100 includes an electronic controller 200.

As most easily seen at FIG. 2, the heater assembly 106 is shown as including a tubular outer heat shield 108, a combustion chamber outer shell 110, and a combustion chamber inner shell 112. When assembled, the outer heat shield 108, the outer shell 110, and the inner shell 112 are coaxially aligned and arranged such that the inner shell 112 is located within and spaced from the outer shell 110 and such that the inner shell 112 and the outer shell 110 reside within and are spaced from the tubular outer heat shield 108. With such an orientation, a first interstitial space or air gap is formed between the inner shell 112 and the outer shell 110 and a second interstitial space or gap is formed between the outer shell 110 and the heat shield 108. Stand-offs or other support structures can be provided to support the outer shell 110 within the heat shield 108 and to support the inner shell 112 within the outer shell 110. In the example shown, the tubular outer heat shield 108 is formed from a first half shell 108a and a second half shell 108b, while the inner shell 112 and the outer shell 110 are each formed from a single sheet welded at a seam. Other configurations are possible.

The heater assembly 106 is also shown as including a rear ring 118 mounted at an inlet end of the combustion chamber inner shell 112 and a front ring 119 mounted at the opposite end of the shell 110. The rear ring 118 supports a burner assembly 120 which is shown as including an air pump 140, a burner mount 122, a nozzle head assembly 124, and a mixer or blender 125. The nozzle head assembly 124 is secured to the burner mount 122 with the burner mount 122 including an ignitor and other control components. The nozzle head assembly includes a fuel inlet port that is connected to a fuel line 126, which in turn extends to a fuel intake assembly 128. As shown, the fuel intake assembly 128 extends through and is secured at an opening 102b in the fuel tank 102 and extends into the interior volume 102a of the fuel tank 102. The fuel intake assembly 128 is shown as including a fuel filter 130 at an inlet end 128a of the fuel intake assembly 128 and a main tube 132. A tank heater 134, inserted through opening 102c, may also be provided. The heater assembly 106 is also shown as including a fan 138 for drawing air through an intake grille 136, and through the first interstitial space or gap 114 between the shell 112 and the outer shell 110 such that heated air is provided in a forced air arrangement. In the example shown, the fan 138 is driven by an electric motor 206 and the air pump 140 is driven by an electric motor 206a. In an alternative arrangement, the air pump 140 is a rotary vane type pump directly driven by the motor 138, for example, as shown in FIGS. 4-5 and in U.S. Publication 2021/0396139 published on Dec. 23, 2021 and entitled "Rotary Vane Pump", the entirety of which is incorporated by reference herein.

In one aspect, the heater 100 can be operated by an electronic controller 200, as schematically shown at FIG. 1. The electronic controller 200, in part, enables an operator to activate the unit via a power switch 208 and select a space temperature setpoint via a thermostat 209.

Figure 3:
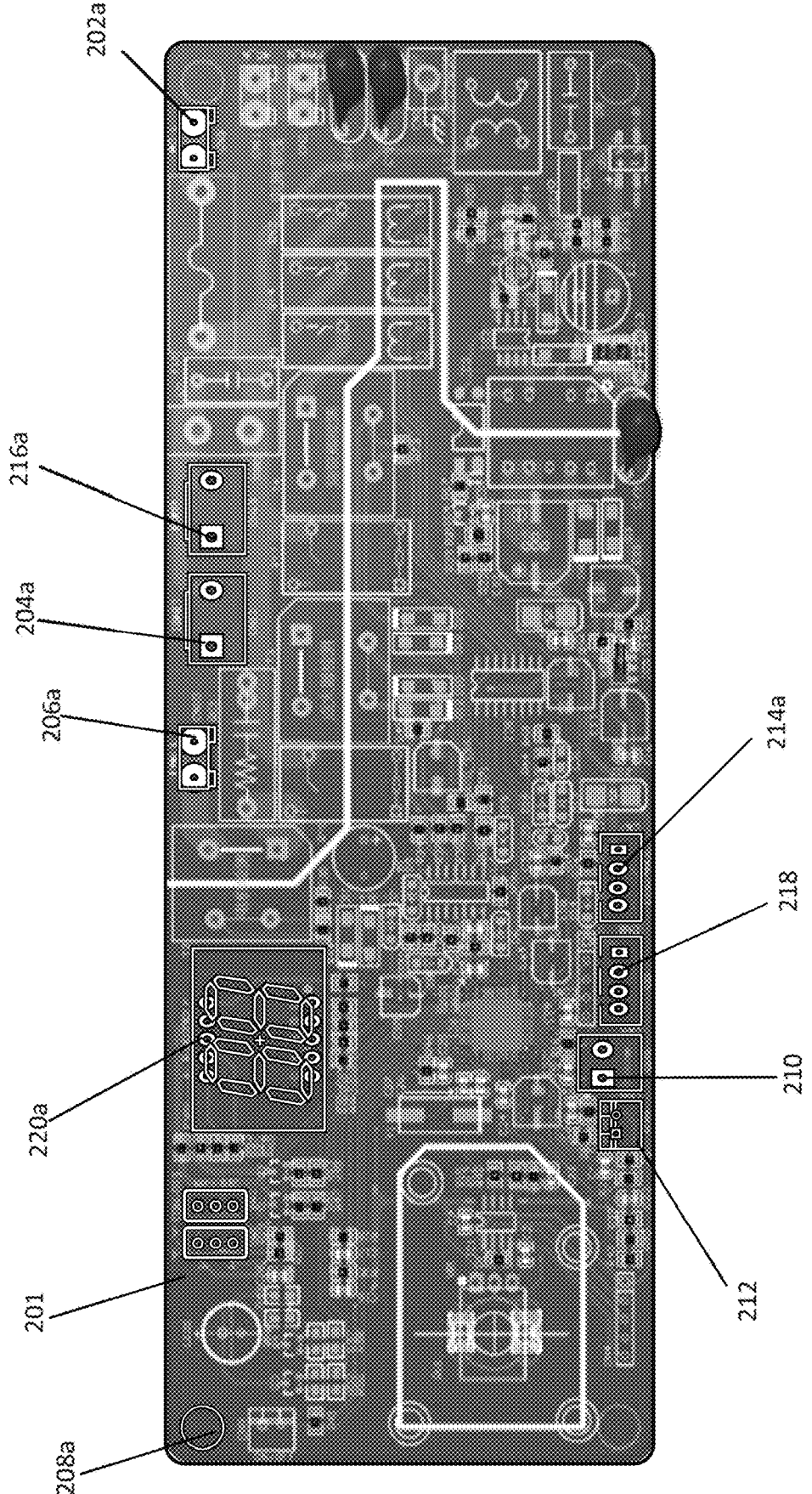
FIG. 3 is an electronic controller of the portable heater of FIG. 1, configured as a printed circuit board.
Figure 4:
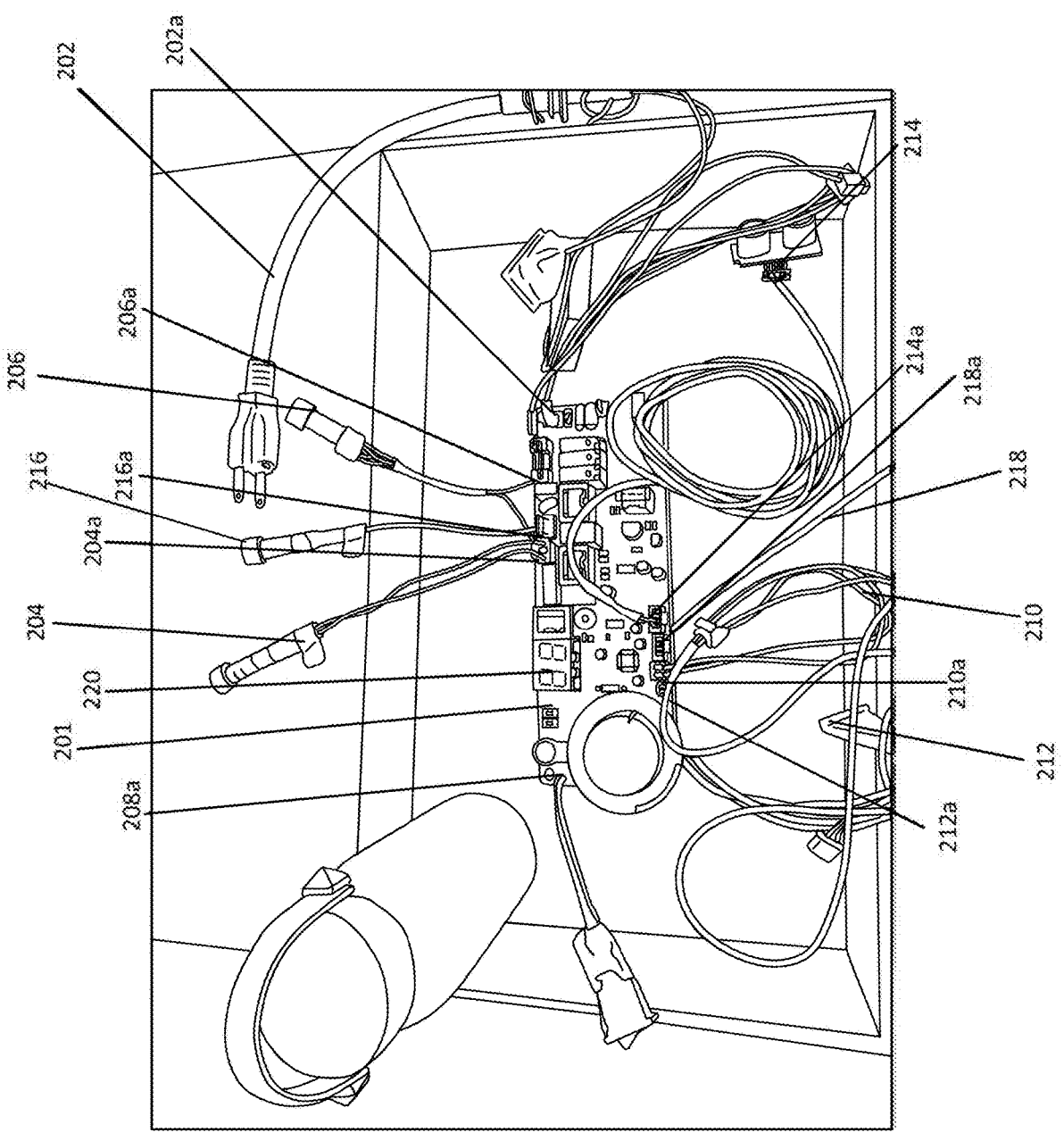
FIG. 4 is the electronic controller of FIG. 3 with various components attached to the electronic controller.
Figure 5:
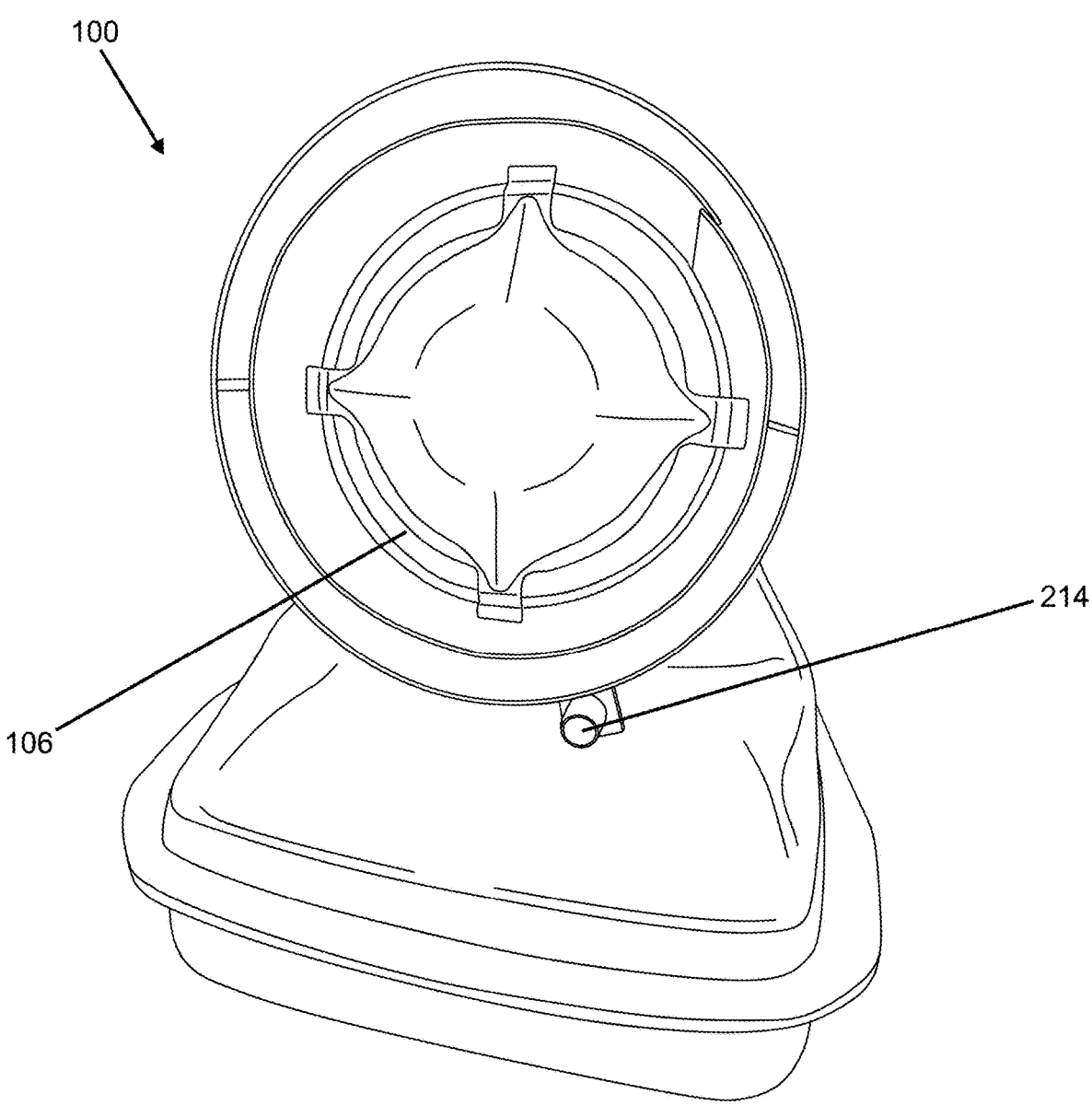
FIG. 5 is a front view of an example portable heater including a proximity sensor.

In some examples, as shown in FIGS. 3-4, the electronic controller 200 includes a printed circuit board (PCB) 201. PCBs have a laminated sandwich structure of conductive and insulating layers. The main function of the PCB first is to affix electrical components in designated locations on the outer layers of the PCB by soldering. The second function is to provide electrical connections between the component's terminals in a manner often referred to as PCB design. Each of the conductive layers is designed with a pattern of conductors (the conductors are similar to wires on a flat surface) that provides electrical connections on that conductive layer. The electronic controller 200 is shown including various ports for inputs and outputs discussed below.

FIG. 3 shows the PCB 201 with no elements attached, highlighting the ports for mounting the inputs and outputs as discussed above. FIG. 4 shows the PCB 201 with the input and output elements attached. A power input 202 connects to the electronic controller 200 at a port 202a. The electronic controller 200 includes a port 208a which is attached to the on-and-off power switch 208. The power switch 208 is configured to power on the power input 202 or power off the power input 202. Other ports on the electronic controller 200 are configured to receive power from the power input 202. The electronic controller 200 includes an igniter port 204a which is used to power an ignitor 204. The electronic controller 200 additionally includes a motor port 206a which is used to power the motors 206, 206a. In some examples the motor 206 powers the fan 138 and the air pump 140, such that only one motor 206 is powered, as is shown at FIGS. 5-8. The motor 206 can also power other elements. The PCB 201 additionally includes a port 220a for a display 220 for, in part, displaying status and error codes.

The electronic controller 200 further includes ports which connect to various safety features. In some examples, the safety features include types of resistors that are capable of changing resistance, where when the resistance is high enough the circuit on the electronic controller 200 is broken and power from the power input 202 to at least some components is stopped. In other examples, the resistance is communicated to a processor 200*a* and instructions from a memory 200*b* are issued to the processor 200*a* depending on the values communicated from the resistor. In some examples the resistor is a photocell 210 attached at port 210*a*. The photocell 210 is a passive element that is a resistor and changes resistance depending on the amount of light incident on the photocell 210. In one example, the photocell 210 is a cadmium sulfoselenide (CDS) photocell. The electronic controller 200 additionally includes a port 212*a* which attaches to a thermistor 212. The thermistor 212 is a resistor wherein the resistance is correlated to the temperature of the thermistor 212. If the thermistor 212 is heated above a temperature, the resistance increases and breaks the circuit of the electronic controller 200. The electronic controller 200 also includes a port 218*a* to attach to a fuel shut-off valve 216, for example a solenoid valve, located in the fuel line 126 such that fuel flow can be shut off by the fuel shut-off valve 216. The electronic controller 200 additionally includes a port 214*a* for a proximity sensor 214 and a port 216*a* for a CO sensor 218. In some examples, the fuel shut-off valve 216 is a spring-biased solenoid valve that is in a normally closed position and is energized open by the electronic controller. In some examples, the fuel shut-off valve 216 is a normally open valve and is energized by the electronic controller to a closed position.

As can be seen at FIG. 4, the electronic controller 200 includes a plug as the power input 202. Other power inputs are additionally possible. For example, the control and outputs/inputs thereof are battery powered in some examples.

Figure 6:
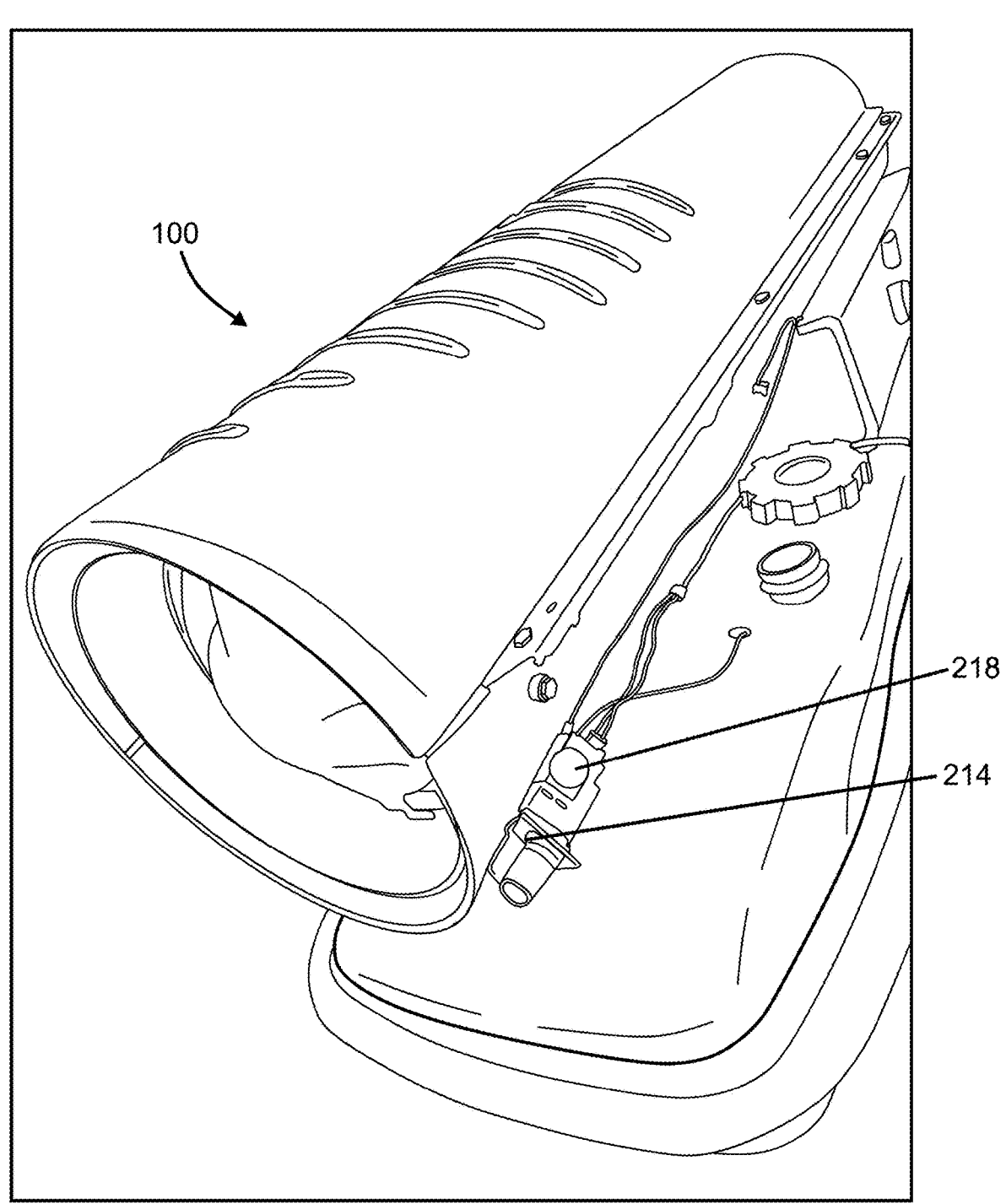
FIG. 6 is a side view of the portable heater of FIG. 5.
Figure 7:
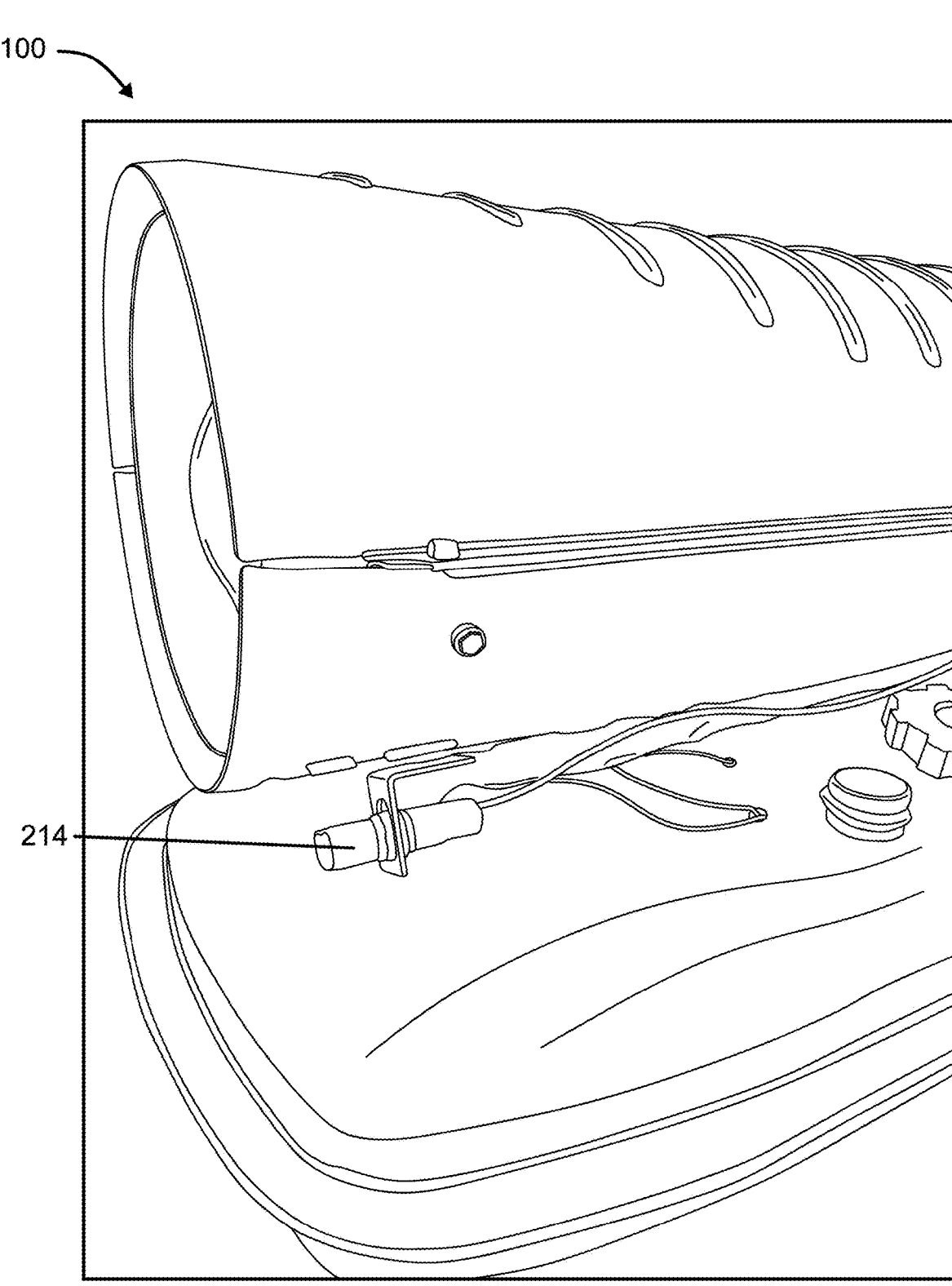
FIG. 7 is a side view of the portable heater of FIG. 8.

In operation, the portable heater 100 can include one or more of the safety features discussed above, for example as shown at FIGS. 1-2 and 5-8. For example, the portable heater 100 can include the proximity sensor 214 in a forward-facing direction mounted to the outer shell of the housing and above the fuel tank 102, for example as shown at FIGS. 5-7. In the particular example shown, the proximity sensor 214 is mounted to the lower half of the outer shell of the housing such that the sensor 214 is located vertically between at least a portion of the outer shell and the fuel tank in a generally protected area of the heater 100. In the example shown, the proximity sensor 214 includes an L-shaped bracket mounted to the housing wherein the sensor probe is mounted to the L-shaped bracket. Other mounting locations, such as to the fuel tank, are possible. The proximity sensor 214 detects when a person or object is at a predetermined distance away from the proximity sensor 214 and the front of the housing that it is unsafe for a predetermined amount of time. The predetermined distance and time are changeable depending on the desired use. Once a person or object is detected, the proximity sensor 214 communicates to the electronic controller 200 to commence a shut-off operation. In some examples, the proximity sensor 214 communicates with the electronic controller 200 to create a warning noise such as an audible beep. In some examples, after beeping for a predetermined amount of time, the electronic controller issues a shut-off signal which shuts off the portable heater 100 and an error code flashes on the display 220. Other embodiments are additionally possible such as directly shutting off the portable heater 100 after a predetermined time and proximity without a warning signal. In some examples the proximity sensor 214 is an infrared proximity sensor 214. In other examples, the proximity sensor 214 is an ultrasonic proximity sensor 214. In some examples, the predetermined distance is 0.5 to 1.5 feet from the proximity sensor 214. In other examples, the predetermined distance is 0 to 0.5 feet from the proximity sensor 214. In the example shown at FIG. 6, the CO sensor is 218 is mounted to the exterior of the heater 100 at a common location with the proximity sensor 214.

Figure 8:
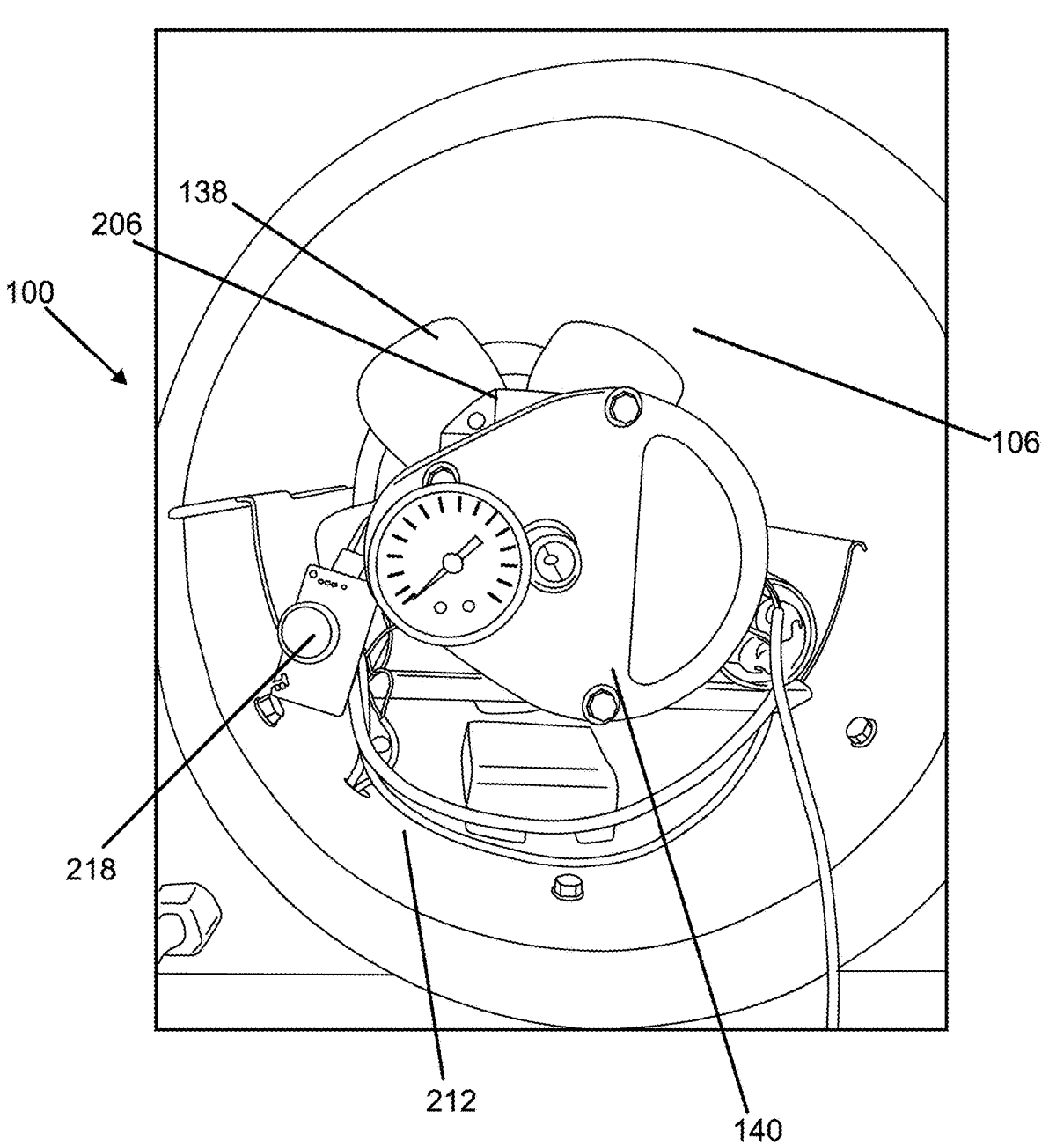
FIG. 8 is a rear/intake view of the portable heater of FIG. 5 including a CO sensor and a temperature sensor.

Referring to FIG. 8, the portable heater 100 is shown as including the CO sensor 218 and the temperature sensor (e.g., a thermistor) 212. In this example, the CO sensor 218 is mounted inside of the heater assembly 106. In some embodiments, the CO sensor detects when carbon monoxide is above a threshold and shuts off the portable heater 100 along with flashing an error code on the display 220. In other examples, the threshold is 50-200 PPM CO. In some examples the PCB additionally includes an input for a VOC sensor.

In some examples, when the thermistor 212 or thermostat reaches above a predetermined temperature threshold, the electronic controller activates the fuel shut-off valve 216 and deactivates the fan motor 206 and ignitor 204. In some examples, after the electronic controller 200 activates the fuel shut-off valve 216, the electronic controller delays deactivation of the motor 206 and/or ignitor 204 for a predetermined amount of time. In some examples, the predetermined amount of time is 180 seconds. This delay enables the fan 138 to continue to provide airflow through the heater assembly 106 such that the internal components can be cooled. The electronic controller 200 can continue to measure the ambient temperature after the fan 138 is shut off and resume operation when the ambient temperature falls below a predetermined threshold, whereby the fuel-shut off valve 216 is deactivated and the motor 206 and ignitor 204 are activated.

In some embodiments, the portable heater 100 includes the photocell 210. The photocell 210 can be placed within the heater assembly 106 to capture the light from a flame within the portable heater 100. The photocell 210 is capable of determining the size or brightness of the flame. In some embodiments, if the flame is too small or not present the electronic controller 200 issues an error message and shuts off the portable heater 100. In other examples, if the flame is too large, the electronic controller 200 issues an error message to the display 220 and shuts off the portable heater 100.

In some embodiments, the CO sensor 218, the temperature sensor 212, the photocell 210, and the proximity sensor 214 are all coupled to the electronic controller 200. In other examples, only the CO sensor 218 and proximity sensor 214 are coupled to the electronic controller 200. Any configuration including or not including any of the CO sensor 218, thermometer (or thermistor 212), photocell 210, and proximity sensor 214 are possible depending on the desired configuration of the portable heater 100.

Figure 9:
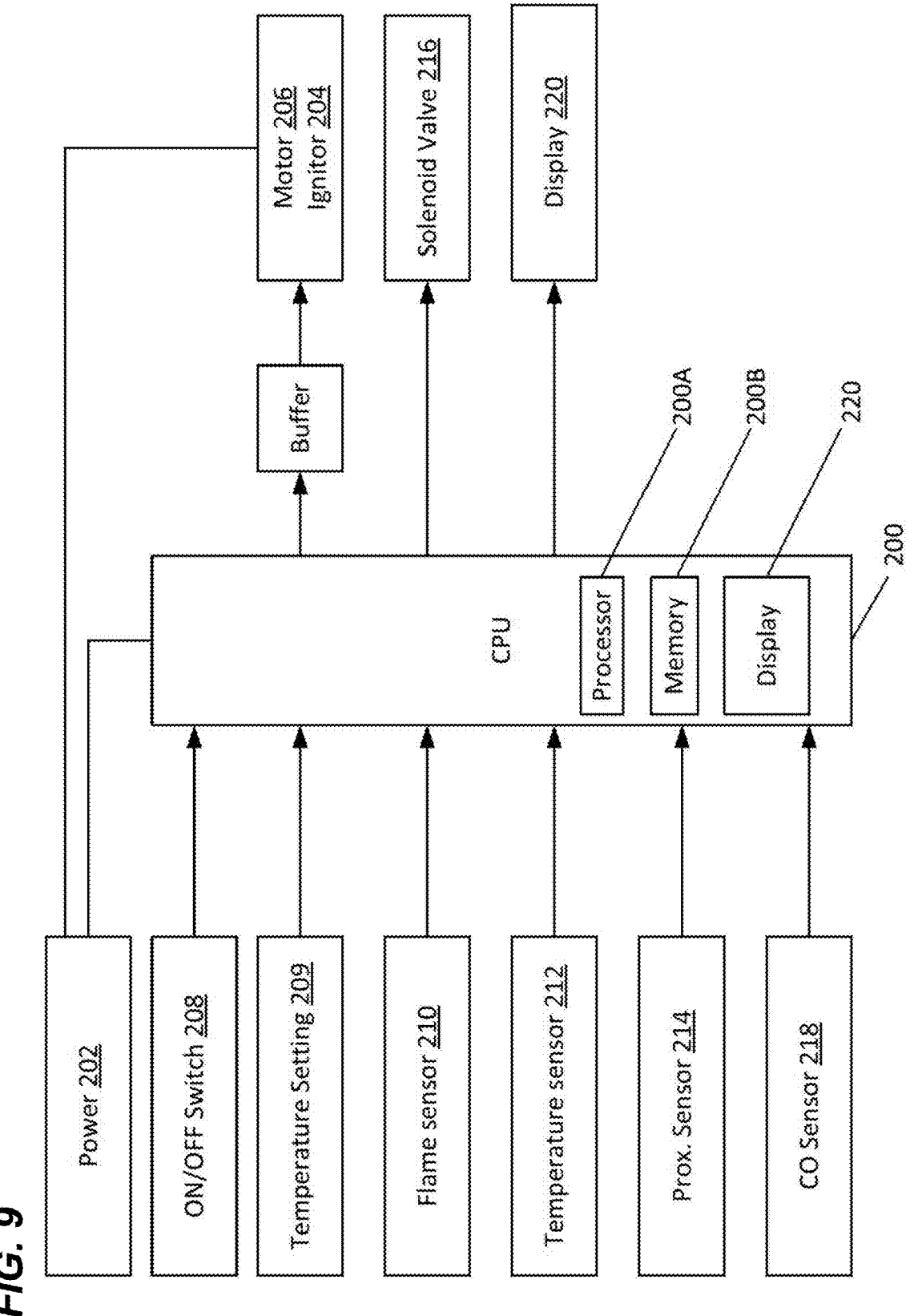
FIG. 9 is a schematic view of an electronic controller functional block diagram in accordance with the principles of the present disclosure.

In reference to FIG. 9, the electronic controller 200 is schematically shown as a functional block diagram and is shown as including a processor 200*a* and a non-transient storage medium or memory 200*b*, such as RAM, flash drive or a hard drive. Memory 200*b* is for storing executable code, the operating parameters, and from various inputs while processor 200*a* is for executing the code.

The electronic controller 200 typically includes at least some form of memory 200B. Examples of memory 200*b* include computer readable media. Computer readable media includes any available media that can be accessed by the processor 200a. By way of example, computer readable media include computer readable storage media and computer readable communication media.

Computer readable storage media includes volatile and nonvolatile, removable and non-removable media implemented in any device configured to store information such as computer readable instructions, data structures, program modules or other data. Computer readable storage media includes, but is not limited to, random access memory, read only memory, electrically erasable programmable read only memory, flash memory or other memory technology, compact disc read only memory, digital versatile disks or other optical storage, magnetic cassettes, magnetic tape, magnetic disk storage or other magnetic storage devices, or any other medium that can be used to store the desired information and that can be accessed by the processor 200a.

Computer readable communication media typically embodies computer readable instructions, data structures, program modules or other data in a modulated data signal such as a carrier wave or other transport mechanism and includes any information delivery media. The term "modulated data signal" refers to a signal that has one or more of its characteristics set or changed in such a manner as to encode information in the signal. By way of example, computer readable communication media includes wired media such as a wired network or direct-wired connection, and wireless media such as acoustic, radio frequency, infrared, and other wireless media. Combinations of any of the above are also included within the scope of computer readable media.

The electronic controller 200 is also shown as having a number of inputs/outputs that may be used to power components of the heater assembly 106 or are safety features, as previously described. As shown at FIG. 9, the electronic controller 200 includes outputs for a motor 206, an ignitor 204, a display 220 and a fuel shut-off valve 216. The electronic controller 200 additionally includes inputs for a thermistor 212, a photocell 210, a proximity sensor 214, and a CO (carbon monoxide) sensor 218. As also shown at FIG. 9, the electronic controller 200 includes inputs for power 202, an on/off switch 208, a thermostat temperature setting 209, a photocell 210 (i.e., flame sensor), a temperature sensor 212, a proximity sensor 214, and a CO sensor 218. The electronic controller 200 is powered at the power input 202. The electronic controller 200 is capable of controlling the power flowing to the outputs depending on the information received by the inputs.

Figure 10:
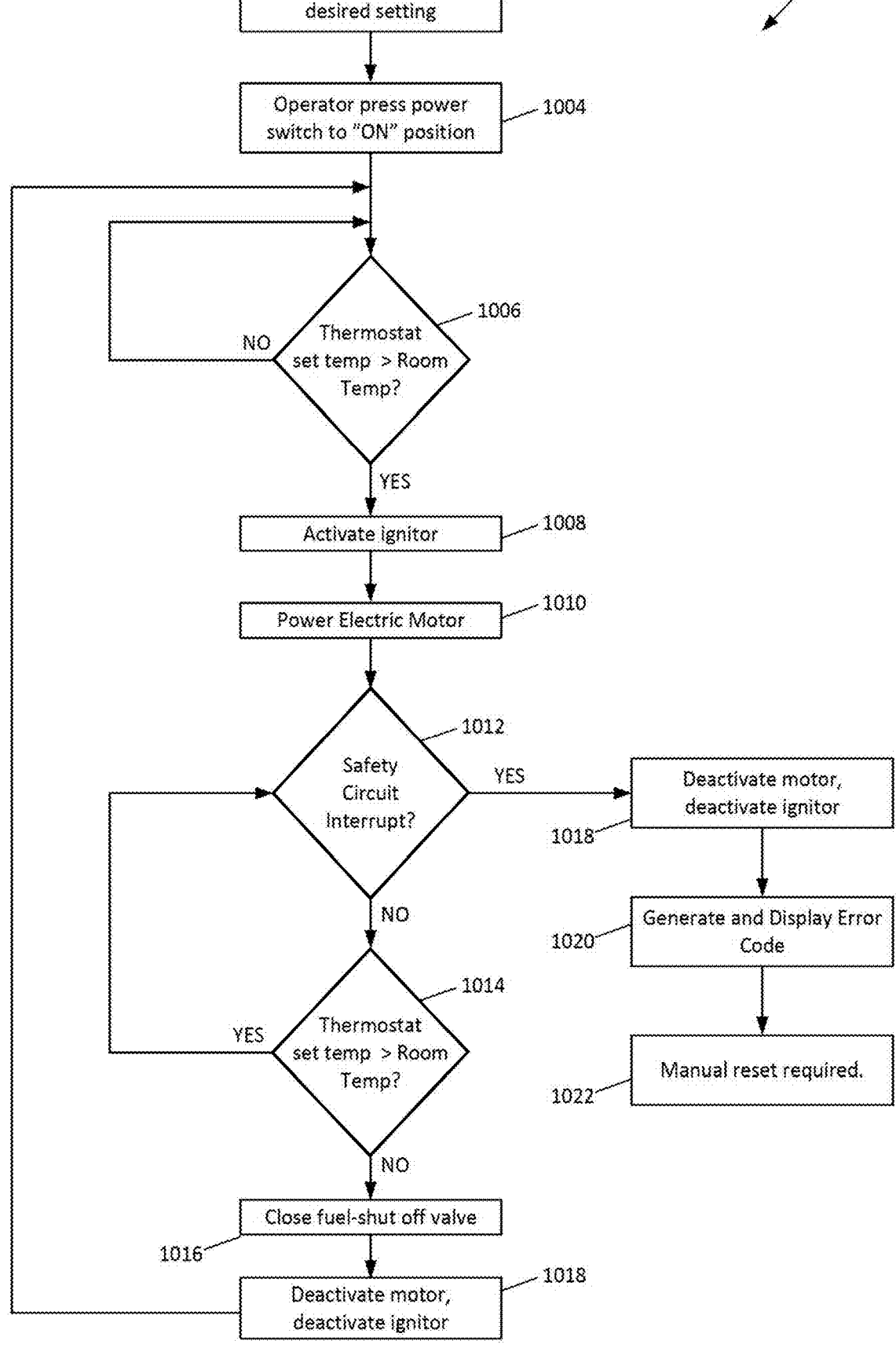
FIG. 10 is a flow chart illustrating how the electronic controller of FIG. 3 functions.

Referring to FIG. 10, an example process flow chart 1000 is presented which illustrates the above-described functions of the electronic controller 200. In a step 1002, an operator sets the thermostat setting to the desired temperature. In a step 1004, the operator activates the power switch for the heater. In a step 1006, the electronic controller determines whether there is a call for heat by comparing the room temperature sensed by the temperature sensor/thermistor to the thermostat setting. When a condition is sensed that the room temperature is below the thermostat setting, the electronic controller activates the ignitor at step 1008 and the fan and air pump motor at step 1010. These steps can be performed at the same time or sequentially, as preferred. At a step 1012, it is determined whether a safety interrupt has occurred. If no, interrupt, the electronic controller continues to monitor whether there is a call for heat at step 1014. If no call for heat exists, such as when the room temperature is at or below setpoint, the fuel shut-off valve is closed at step 1016 and the motor and ignitor are subsequently shut off at step 1018. As related above, a predetermined delay can be incorporated between steps 1016 and 1018.

Figure 11:
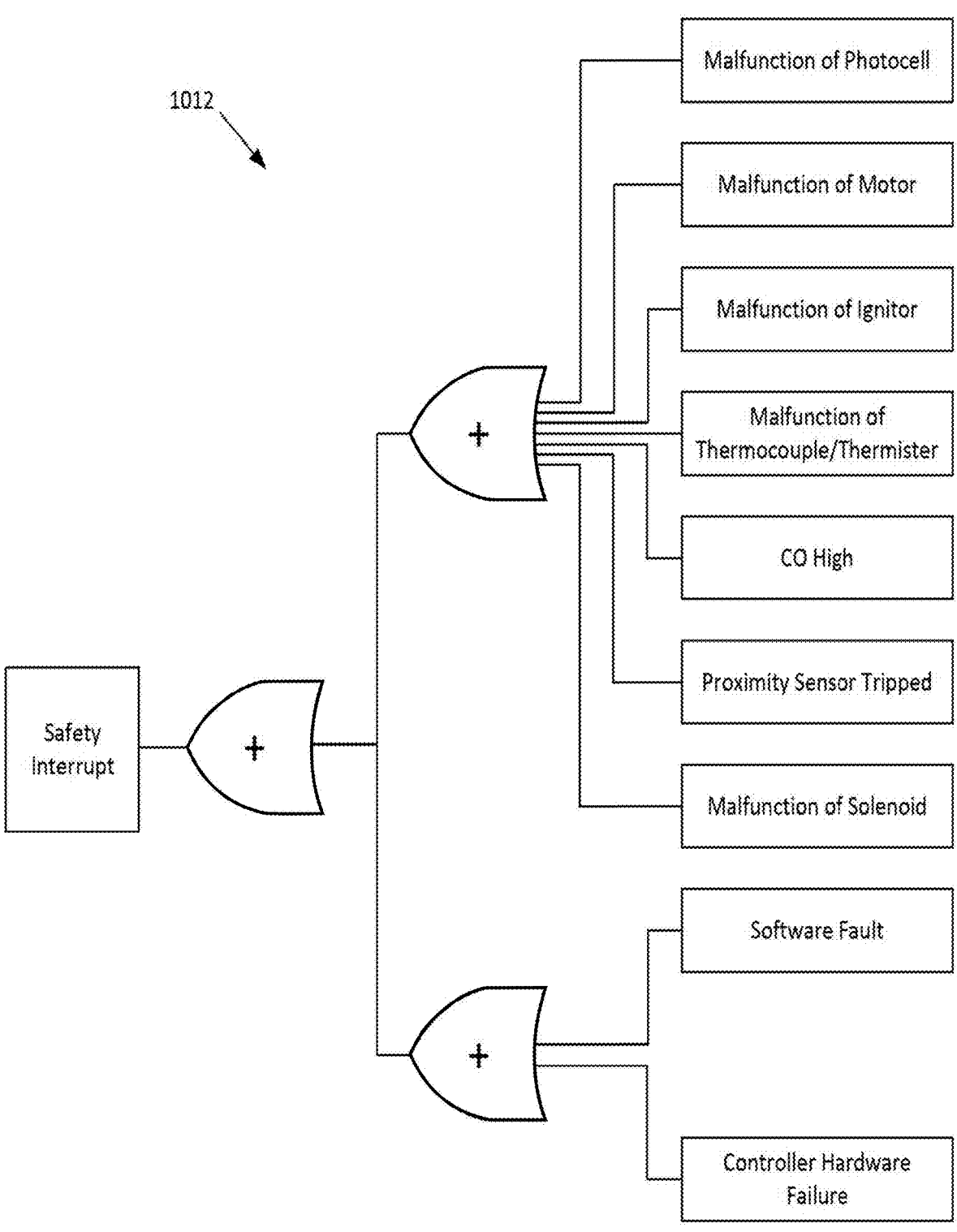
FIG. 11 is a block diagram of how the electronic controller of FIG. 3 functions.

Referring to FIG. 11, an example safety interrupt circuit or algorithm 1012 for the electronic controller is illustrated in which a safety interrupt signal is generated upon any of the following conditions: malfunction of the photocell CDS, malfunction of the motor, malfunction of the ignitor, malfunction of the thermocouple, high carbon monoxide sensed at the CO sensor, proximity sensor tripped, malfunction of the fuel shut-off valve/solenoid valve, a software fault, and an electronic controller hardware failure. Other conditions may be added to trigger a safety interrupt. Referring back to FIG. 11, when there is a safety circuit interrupt at step 1012, the electronic controller deactivates the motor and ignitor at 1018, generates and displays an error code at 1020, and requires a manual reset of the system at step 1022. In one aspect, the electronic controller can be configured to activate the fuel shut-off valve and delay the deactivation of the motor and ignitor for only selected faults or for all faults. For example, the electronic controller can be selectively configured such that, when the proximity sensor detects an object triggering a safety circuit required shut down, the fuel shut-off valve 216 is immediately closed while the electric motor continuous to run for 180 seconds and then shuts off in a normal shut-down sequence, or can configured such that the electric motor is stopped immediately. Similarly, when the CO sensor detects high CO levels, a normal shut-down sequence can be used in which the fuel-shut off valve is first activated/closed and the motor/ignitor are deactivated after a delay, or an alternative approach can be used in which the motor is stopped immediately.

Figure 12:
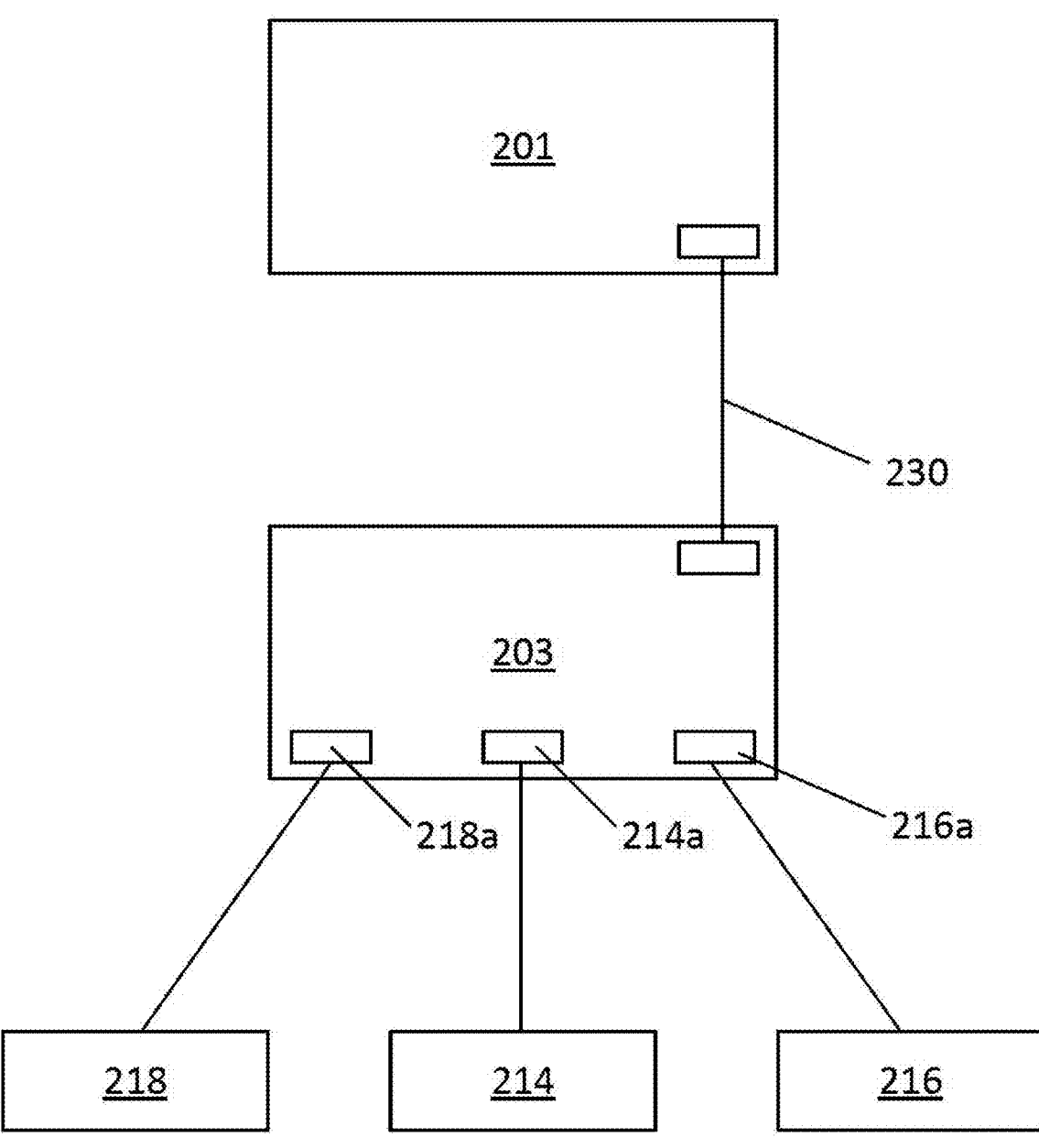
FIG. 12 is a schematic showing an alternative control configuration in which multiple printed circuit boards are used for the electronic controller of the portable heater of the previous figures.

Referring to FIG. 12, an alternative configuration is provided in which the electronic controller is provided with a second printed circuit board 203, configured as an adapter, which receives inputs from the proximity sensor 214 and the CO sensor 218, via a connector such as a connectorized cable 230, and sends an output to the fuel shut-off valve 216. In one aspect, the printed circuit board 203 is connected to and communicates with the printed circuit board 201. In this way, an electronic controller 200 with a circuit board 201 can be provided with the additional functionality provided by the sensors 214, 218 and fuel shut-off valve 216 by adding circuit board 203. In one aspect, the printed circuit boards 201 and 203 are CSA Group certified. In one aspect, printed circuit board 203 (or 201 when 203 is note used) is configurable, through switches or programing, to select whether one or both of the CO sensor 218 and proximity sensor 214 are used in a particular configuration such that the same PCB 201 and/or 203 can be used for CO only installations, proximity only installations, and installations including both CO and proximity sensors. In some examples, the PCB 201/203 is provided with plug in locations 218a, 214a, 216a that automatically select the configuration based on whether a connection has been made at that particular location. PCB 201 and/or 203 can also be configured to send error codes in the event of a fault condition. In some example configurations for PCB 201 and/or 203, and with respect to the CO sensor 218, the heater 100 can be shut down when CO is above a threshold setting (e.g., 50 ppm) in which the heater 100 is shut down and an error code is generated. A VOC sensor can also be integrated into PCB 203 as already described above for PCB 201. In some example configurations for PCB 201 and/or 203, and with respect to the proximity sensor 214, an audio warning is generated via a component mounted to or in communication with the PCB. In one example sequence, the PCB 201 and/or 203 generates an audio warning at 1 beep per second when an object presents within 1.5 to 2 feet distance from the burner outlet for more than 5 seconds, generates an audio warning at 3 beeps per second when an object presents within 0.5 to 1.5 feet range from the burner outlet, and generates an audio warning and immediately shuts down the heater 100 when an object presents within 0.5 to 0 feet distance from the heater burner outlet. In some examples, a flashing light can be used instead of or in conjunction with the audio warning.

From the forgoing detailed description, it will be evident that modifications and variations can be made in the aspects of the disclosure without departing from the spirit or scope of the aspects. While the best modes for carrying out the many aspects of the present teachings have been described in detail, those familiar with the art to which these teachings relate will recognize various alternative aspects for practicing the present teachings that are within the scope of the appended claims.

What is claimed is:

1. A fuel-fired heater comprising:
   a) a fuel tank;
   b) a housing assembly supported by the fuel tank, the housing assembly defining a chamber having an air inlet and an air outlet;
   c) a fan located within the housing assembly;
   d) an air pump located within the housing assembly;
   e) an electric motor coupled to at least one of the fan and the air pump;
   f) a burner assembly located within the housing assembly, the burner assembly including a burner nozzle in fluid communication with the air pump and the fuel tank via a fuel line, and including an ignitor; and
   g) an electronic controller operating the electric motor and the ignitor, the electronic controller including a proximity sensor oriented and arranged to sense an object located in front of the air outlet, wherein the electronic controller deactivates the electric motor when an object is sensed by the proximity sensor within a predetermined distance for a predetermined time period.

2. The fuel-fired heater of claim 1, further comprising:
   a) a fuel shut-off valve oriented and arranged to control fuel flow in the fuel line, wherein the electronic controller deactivates the heater by first causing the fuel shut-off valve to block flow through the fuel line and subsequently deactivating the electric motor after a predetermined time period.

3. The fuel-fired heater of claim 2, further comprising:
   a) a carbon monoxide sensor oriented and arranged to sense an ambient carbon monoxide level proximate the heater, wherein the electronic controller causes the fuel shut-off valve to close when a sensed carbon monoxide level exceeds a predetermined threshold for a predetermined period of time and subsequently deactivating the electric motor after a predetermined time period.

4. The fuel-fired heater of claim 3, wherein the predetermined threshold is 50-200 parts per million of carbon monoxide.

5. The fuel-fired heater of claim 3, wherein the predetermined time period is between one and five minutes.

6. The fuel-fired heater of claim 3, wherein the predetermined time period is about three minutes.

7. The fuel-fired heater of claim 2, wherein the electronic controller immediately closes the fuel shut-off valve when an object is sensed by the proximity sensor at a distance between 0 and 0.5 feet from the housing assembly air outlet.

8. The fuel-fired heater of claim 1, wherein the proximity sensor is mounted to the housing assembly.

9. The fuel-fired heater of claim 1, wherein the electronic controller generates an audio warning when an object is sensed by the proximity sensor at a first predetermined distance.

10. The fuel-fired heater of claim 9, wherein the first predetermined distance is within 0.5 to 1.5 feet of the housing assembly air outlet.

11. The fuel-fired heater of claim 1, wherein the proximity sensor is an ultrasound or infrared type proximity sensor.

12. A fuel-fired heater comprising:
   a) a fuel tank;
   b) a housing assembly supported by the fuel tank, the housing assembly defining a chamber having an air inlet and an air outlet;
   c) a fan located within the housing assembly;
   d) an air pump located within the housing assembly;
   e) an electric motor coupled to at least one of the fan and the air pump;
   f) a burner assembly located within the housing assembly, the burner assembly including a burner nozzle in fluid communication with the air pump and the fuel tank via a fuel line, and including an ignitor;
   g) a fuel shut-off valve oriented and arranged to control fuel flow in the fuel line; and
   h) an electronic controller operating the electric motor, the ignitor, and the fuel shut-off valve, the electronic controller including a shut-down sequence in which the electronic controller deactivates the heater by first activating the fuel shut-off valve to block flow through the fuel line and subsequently deactivating the electric motor after a predetermined time period.

13. The fuel-fired heater of claim 12, wherein the predetermined time period is between one and five minutes.

14. The fuel-fired heater of claim 13, wherein the predetermined time period is about three minutes.

15. The fuel-fired heater of claim 13, further comprising:
   a) a proximity sensor oriented and arranged to sense an object located in front of the air outlet, wherein the electronic controller activates the shut-down sequence or immediately deactivates the electric motor when an object is sensed by the proximity sensor within a predetermined distance for the predetermined time period.

16. The fuel-fired heater of claim 15, wherein the proximity sensor is mounted to the housing assembly.

17. The fuel-fired heater of claim 15, wherein the electronic controller generates an audio warning when an object is sensed by the proximity sensor at a first predetermined distance.

18. The fuel-fired heater of claim 15, wherein the proximity sensor is an ultrasound or infrared type proximity sensor.

19. The fuel-fired heater of claim 12, further comprising:
   a) a carbon monoxide sensor oriented and arranged to sense an ambient carbon monoxide level proximate the heater, wherein the electronic controller activates the shut-down sequence when a sensed carbon monoxide level exceeds a predetermined threshold for a predetermined period of time.

20. The fuel-fired heater of claim 19, wherein the predetermined threshold is 50-200 parts per million of carbon monoxide.

* * * * *